(12) United States Patent
Kellerman et al.

(10) Patent No.: US 8,168,597 B2
(45) Date of Patent: May 1, 2012

(54) METHOD FOR TREATING CYSTIC FIBROSIS

(75) Inventors: Donald J. Kellerman, San Jose, CA (US); Ramesh Krishnamoorthy, Cary, NC (US); José L. Boyer, Chapel Hill, NC (US); Amy E. Schaberg, Cary, NC (US)

(73) Assignee: Inspire Pharmaceuticals, Inc., Whitehouse Station, NJ (US)

( * ) Notice: Subject to any disclaimer, the term of this patent is extended or adjusted under 35 U.S.C. 154(b) by 230 days.

(21) Appl. No.: 12/603,506

(22) Filed: Oct. 21, 2009

(65) Prior Publication Data

US 2010/0099635 A1    Apr. 22, 2010

Related U.S. Application Data

(60) Provisional application No. 61/107,574, filed on Oct. 22, 2008.

(51) Int. Cl.
*A61K 31/70* (2006.01)
*A01N 43/04* (2006.01)
*C07H 17/08* (2006.01)
*C07H 19/00* (2006.01)

(52) U.S. Cl. ............... 514/28; 514/30; 514/51; 536/7.2; 536/26.22

(58) Field of Classification Search ......................... None
See application file for complete search history.

(56) References Cited

U.S. PATENT DOCUMENTS

| | | | |
|---|---|---|---|
| 4,977,263 A | 12/1990 | Schriewer et al. | |
| 5,837,861 A * | 11/1998 | Pendergast et al. | 536/25.6 |
| 6,348,589 B1 * | 2/2002 | Pendergast et al. | 536/25.6 |
| 6,596,725 B2 * | 7/2003 | Peterson et al. | 514/256 |
| 6,624,150 B2 * | 9/2003 | Yerxa et al. | 514/47 |
| 6,673,779 B2 * | 1/2004 | Jacobus et al. | 514/51 |
| 6,696,425 B2 * | 2/2004 | Yerxa et al. | 514/47 |
| 6,818,629 B2 * | 11/2004 | Peterson et al. | 514/47 |
| 6,864,243 B1 * | 3/2005 | Peterson | 514/47 |
| 7,018,985 B1 * | 3/2006 | Boyer et al. | 514/48 |
| 7,078,391 B2 * | 7/2006 | Peterson et al. | 514/47 |
| 7,101,860 B2 * | 9/2006 | Boyer et al. | 514/43 |
| 7,223,744 B2 * | 5/2007 | Yerxa et al. | 514/47 |
| 7,256,183 B2 * | 8/2007 | Peterson et al. | 514/47 |
| 7,531,525 B2 * | 5/2009 | Yerxa et al. | 514/51 |
| 2003/0129140 A1 | 7/2003 | Tarara et al. | |
| 2008/0057129 A1 | 3/2008 | Lerner et al. | |
| 2008/0066741 A1 | 3/2008 | LeMahieu et al. | |

FOREIGN PATENT DOCUMENTS

WO    WO 2004/069253 A1    8/2004
WO    WO 2007/090646 A1    8/2007

OTHER PUBLICATIONS

Amsden, G. W., "Anti-inflammatory effects of macrolides—an underappreciated benefit in the treatment of community-acquired respiratory tract infections and chronic inflammatory pulmonary conditions?" *J. Antimicrobial Chemo*, (2005) 55, 10-21.
Ashlock et al., "A pipeline of Therapies for Cystic Fibrosis," *Semin Respir Crit Care Med.*, 2009, 30:611-626; Thieme Medical Publishers, Inc., New York, NY 10001.
Bendiak & Ratjen, "The approach to *Pseudomonas aeruginosa* in cystic fibrosis," *Semin Respir Crit Care Med*. 2009; 30:587-595. Thieme Medical Publishers, Inc., New York, NY 10001.
Capitano et al., "Steady-State Intrapulmonary Concentrations of Moxifloxacin, Levofloxacin, and Azithromycin in Older Adults" *Chest* (2004) 125(3): 965-973.
Deterding, et al., "Safety and Tolerability of Denufosol Tetrasodium Inhalation Solution, a Novel $P2Y_2$ Receptor Agonist" *Pediatric Pulm* (2005) 39: 339-348.
Ekici et al., "Effect of Azithromycin on the Severity of Bronchial Hyperresponsiveness in Patients with Mild Asthma" *J. Asthma*, (2002) 39(2): 181-185.
Flume et al., "Cystic Fibrosis Pulmonary Guidelines: Treatment of Pulmonary Exacerbations," *Am J Respir Crit Care Med.*, 2009.
Hickey et al., "Inhaled Azithromycin Therapy." *J. Aerosol Medicine*, (2006) 19(1): 54-60.
Hodge et al., "Azithromycin Improves Macrophage Phagocytic Function and Expression of Mannose Receptor in Chronic Obstructive Pulmonary Disease," *Am J Resp & Crit Care Med*, (2008) 178(2): 139-148.
Inspire Pharmaceuticals, Inc., Press Release Jun. 6, 2008, announcing Achievement of Primary Endpoint in Phase 3 Trial with Denufosol for Cystic Fibrosis.
Kellerman, et al.,"Denufosol: A review of studies with inhaled $P2Y_2$ agonists that led to Phase 3," *Pulm Pharmacol Ther.*, (2008) 21: 600-7.
O'Sullivan & Flume, "The Clinical Approach to Lung Disease in Patients with Cystic Fibrosis," *Semin Respir Crit Care Med.*, 2009, 30:505-513; Thieme Medical Publishers, Inc., New York, NY 10001.
Simpson et al., "Clarithromycin Targets Neutrophilic Airway Inflammation in Refractory Asthma" *Am J Respir Crit Care Med* (2008) 177: 148-155.

(Continued)

*Primary Examiner* — Lawrence E Crane
(74) *Attorney, Agent, or Firm* — Perkins Coie LLP.; Viola T. Kung

(57) ABSTRACT

The present invention is directed to a method for treating cystic fibrosis. The method comprises the steps of: identifying a patient suffering from cystic fibrosis, and administering to the patient an effective amount of denufosol or a pharmaceutically acceptable salt thereof and an effective amount of a macrolide. In one method, denufosol and the macrolide are administered by inhalation, preferably in a single formulation. In another method, denufosol is administered by inhalation and the macrolide is administered orally. The present invention is also directed to a pharmaceutical formulation comprising denufosol or a pharmaceutically acceptable salt thereof, a macrolide, and a pharmaceutically acceptable carrier. Preferred denufosol is denufosol tetrasodium and preferred macrolide is azithromycin. The pharmaceutical formulation preferably is in a form of an inhalable dry powder or in a liquid form.

15 Claims, 2 Drawing Sheets

OTHER PUBLICATIONS

Smiley et al., "Denufosol Tetrasodium Inhalation Solution: Results from Two Phase 2 Trials in CF Patients with Mild to Moderate Lung Disease." CF Europe 2006 Poster.

Smith, "Denufosol Improves Airway Function in Cystic Fibrosis." *MedPage Today*, Medpage Today Action Points, Review, Jun. 6, 2008.

Yerxa, et al., "Pharmacology of INS37217 [$P^1$-(Uridine 5')-$P^4$-(2'-deoxycytidine 5')tetraphosphate, Tetrasodium Salt], a Next-Generation $P2Y_2$ Receptor Agonist for the Treatment of Cystic Fibrosis" *J. Pharmacol Exp Ther.*, (2002) 302: 871-880.

International Search Report for PCT/US09/61556, mailed Dec. 14, 2009.

* cited by examiner

METHOD FOR TREATING CYSTIC FIBROSIS

This application claims the benefit of U.S. Provisional Application 61/107,574, filed Oct. 22, 2008; which is incorporated herein by reference in its entirety.

TECHNICAL FIELD

This invention relates to methods of treating cystic fibrosis by administering denufosol and a macrolide to a patient. This invention also relates to a pharmaceutical formulation comprising denufosol and a macrolide such as azithromycin.

BACKGROUND OF THE INVENTION

Cystic fibrosis (CF) is an autosomal recessive genetic disease, characterized by pulmonary and sinus disease, and gastrointestinal and reproductive tract dysfunction. The disease is caused by mutations in the cystic fibrosis transmembrane regulator (CFTR) gene, which encodes for an apical membrane epithelial protein that functions as a c-AMP-regulated chloride channel and a regulator of other channels. Defective CFTR results in abnormal ion transport and depleted airway surface liquid volume with reduced mucociliary clearance and a propensity for chronic infection of the respiratory tract with resulting inflammation, progressive airway damage and bronchiectasis. CF patients suffer from chronic repeated cycles of pulmonary bacterial colonization, pulmonary exacerbations and chronic lung function decline, which often lead to premature death. Although improved treatment of lung disease has increased survival, the median predicted age for survival is only 35 years, and patients continue to have significant morbidity, including hospitalizations.

Nucleotide $P2Y_2$ agonists, such as uridine 5-triphosphate (UTP) and diquafosol tetrasodium [$P^1$, $P^4$-di(uridine 5'-) tetraphosphate, tetrasodium salt], regulate certain activities of the human airway epithelium. The $P2Y_2$ receptor is abundant on the luminal surface of polarized epithelial cells, especially those lining muscosal surfaces exposed to the external environment. $P2Y_2$ agonists act by stimulating the $P2Y_2$ receptor, which results in the secretion of chloride ion ($Cl^-$) and liquid and the inhibition of sodium ($Na^+$) absorption to hydrate the airway surface liquid layer and to create a more normal periciliary fluid milieu. $P2Y_2$ agonists also act by stimulating mucin secretion from goblet cells and increasing ciliary beat frequency.

$P2Y_2$ receptor agonists represent a new approach to the treatment of CF, which bypasses the defective CFTR chloride channel, and activates an alternative chloride channel. This activation results in an increase in airway surface epithelial hydration, and through these actions and effects on cilia beat frequency, increases mucociliary clearance. Denufosol tetrasodium [$P^1$-(uridine 5'-)-$P^4$-(2'-deoxycytidine 5'-) tetraphosphate, tetrasodium salt], a chemically stable, selective $P2Y_2$ receptor agonist, has been investigated in clinical trial studies as a treatment for patients with CF. (Kellerman, et al., *Pulm Pharmacol Ther.*, 21: 600-7, 2008; Deterding, et al., Pediatric Pulm 39: 339-348, 2005; Yerxa, et al., *J. Pharmacol Exo Ther.*, 302: 871-880, 2002.)

Macrolides are a group of broad spectrum antibiotics. Macrolides include natural macrolides that are produced by various strains of *Streptomyces* (spore forming bacteria that grow slowly in soil or water as a branching filamentous mycelium similar to that of fungi) and man-made macrolides that are similar in structure to the natural macrolides; both groups have a complex chemical (macrocyclic) structure. They act by inhibiting protein synthesis, specifically by blocking the 50S ribosomal subunit.

ZITHROMAX® (azithromycin tablets and azithromycin for oral suspension) is indicated for the treatment of patients with mild to moderate infections caused by susceptible strains of microorganisms producing sexually transmitted diseases such non-gonococcal urethritis and cervicitis due to *Chlamydia trachomatis*. Azithromycin alone or in combination with other drugs is used for the profilaxis and treatment of mycobacterial infections such as disseminated Mycobacterium avium complex (MAC) disease in persons with advanced HIV infection.

Macrolides such as azithromycin when taken orally by patients can have adverse effects related to gastrointestinal, cardiovascular (prolongation of QT interval), genitourinary, nervous system (dizziness and headache), and allergic reaction. Most of the side effects leading to discontinuation of ZITHROMAX® in clinical trials were related to the gastrointestinal tract, e.g., nausea, vomiting, diarrhea, or abdominal pain (ZITHROMAX® Product Insert). Adverse effects of oral azithromycin could potentially interfere with the often impaired delicate gastrointestinal system of patients; thus it could interfere with absorption of nutrient or other concomitant medications that those patients must take every day, including dietary supplements.

There is a need for an improved method for treating cystic fibrosis; such method is not only effective to treat cystic fibrosis but also does not have significant adverse effects.

SUMMARY OF THE INVENTION

The present invention is directed to a method for treating cystic fibrosis. The method comprises the steps of: identifying a patient suffering from cystic fibrosis, and administering to the patient an effective amount of denufosol or a pharmaceutically acceptable salt thereof and an effective amount of a macrolide. Denufosol and the macrolide can be administered either sequentially or by co-administration. Preferred denufosol is denufosol tetrasodium and preferred macrolide is azithromycin, clarithromycin, dirithromycin, erythromycin, or roxithromycin. An effective amount of denufosol is about 100-400 mg per day and an effective amount of a macrolide is 10-200 mg per day.

The present invention is also directed to a pharmaceutical formulation comprising denufosol or a pharmaceutically acceptable salt thereof, a macrolide, and a pharmaceutically acceptable carrier. Preferred denufosol is denufosol tetrasodium and preferred macrolide is azithromycin. The pharmaceutical formulation preferably is in a form of an inhalable dry powder or in a liquid form.

DETAILED DESCRIPTION OF THE INVENTION

Figure 1:
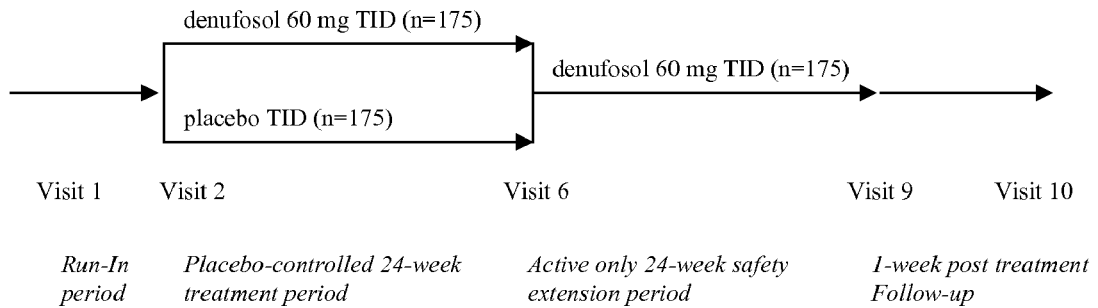
FIG. 1 shows the clinical study schematic.

The inventors have discovered an effective method for treating cystic fibrosis (CF) by administering denufosol and a macrolide to a patient suffering from CF. The inventors have discovered that combined administration of denufosol and a macrolide is more effective in treating CF than the single administration of either denufosol or a macrolide.

The present invention is directed to a method for treating cystic fibrosis. The method comprises the steps of: first identifying a patient suffering from cystic fibrosis, then administering to the patient an effective amount of denufosol or a pharmaceutically acceptable salt thereof and an effective amount of a macrolide. Denufosol is administered to the patient by inhalation. The macrolide is administered to the patient by systemic administration or by local administration.

"An effective amount" as used herein, is meant an amount that has a therapeutic effect, which improves the lung function, as measured by FEV1 of the patient being treated. In the present method, the effective amount of denufosol by inhalation is about 100-400 mg per day, preferably about 120-250 mg per day, or about 150-200 mg per day. In one embodiment, the effective amount of denufosol is about 180 mg per day.

In the present method, an effective amount of a macrolide is about 10-200 mg per day, preferably about 25-150 mg per day, or about 50-100 mg per day. In one embodiment, the effective amount of a macrolide is 500-1000 mg per week.

"About" as used in this application, refers to ±15% of the recited value.

Denufosol

The chemical name of denufosol is $P^1$-(uridine 5'-)-$P^4$-(2'-deoxycytidine 5'-) tetraphosphate; its chemical registry number is 211448-85-0. Denufosol is a $P2Y_2$ receptor agonist, which has the ability to restore or maintain mucociliary clearance in patients relatively early in the CF lung disease process, thus preserving lung function and lessening the inevitable repeat cycles of pulmonary bacterial colonization, pulmonary exacerbations, and chronic lung function decline.

Denufosol of the present invention encompasses its pharmaceutically acceptable salts, such as, but not limited to, an alkali metal salt such as a sodium salt or a potassium salt; a transition metal salt such as a manganese salt; an alkaline earth metal salt such as a magnesium salt or a calcium salt; or an ammonium or tetraalkyl ammonium salt. Pharmaceutically acceptable salts are salts that retain the desired biological activity of the parent compound and do not impart undesired toxicological effects.

Pharmaceutically acceptable salts of denufosol include tetra-(alkali metal) salts, wherein the alkali metal is sodium, potassium, lithium, or the combination thereof. For example, tetra-(alkali metal) salts of denufol include tetrasodium salts, tetrapotassium salts, tetralithium salts, trisodium/monopotassium salts, disodium/dipotassium salts, monosodium/tripotassium salts, trisodium/monolithium salts, disodium/dilithium salts, monosodium/trilithium salts, disodium/monopotassium/monolithium salts, dipotassium/monosodium/monolithium salts, and dilithium/monosodium/monopotassium salts. Tetrasodium salt is a preferred salt.

Other pharmaceutically acceptable salts of denufosol include tetraammonium salts and tetra(quaternary ammonium) salts.

Macrolides

Macrolides are a group of drugs (typically antibiotics) whose activity stems from the presence of a macrolide ring, a large macrocyclic lactone ring to which one or more deoxy sugars, usually cladinose and desosamine, may be attached. The lactone rings are usually 14, 15 or 16-membered.

Macrolides useful for this invention include natural macrolides produced by *Streptomyces* and synthetic macrolides. Suitable macrolides for this invention include known macrolides such as azithromycin, clarithromycin, dirithromycin, erythromycin, roxithromycin, and telithromycin. Suitable macrolides also include those under development such as carbomycin A, josamycin, kitasamycin, oleandomycin, spiramycin, troleandomycin, and tylosin/tylocine.

Routes of Administration

The key of the invention lies in the ability to deliver denufosol and the macrolide in suitably high concentrations to the lungs. Any method of delivering denufosol and macrolide to the lumen of the lung, including local administration and systemic administration, is suitable for the present invention.

Systemic administration is introducing a medicament into the circulation. Examples of systemic administration include oral ingestion, intravenous, subcutaneous, intraperitoneal, intrathecal, or intramuscular administration.

Local administration includes inhalation, topical application, and targeted drug delivery. Methods of inhalation include liquid instillation, inhalation of aerosolized solution or pressurized fluid preparation via nebulizer (most preferred), inhalation of dry powder or a mixture of ingredients in a fluid formulation by inhaler (more preferred), and directing soluble or dried material of soluble or insoluble fractions of a discrete particle size distribution into the air stream during mechanical ventilation (preferred).

An example of targeted drug delivery is enclosure of denufosol, the macrolide, or the combination within a liposome, where the liposome is coated with a specific antibody whose antigen is expressed in the targeted lung tissue. Alternatively, the liposomal preparation can be designed in such a fashion wherein the core of the liposome contains denufosol and the external surface of the liposomal preparation is coated with the macrolide, which is covalently bound to cationically charged moieties that traverse the alveolar surface and bind to the alveolar surface.

Another example of a delivery system includes nanoparticulates or microparticulates compositions of the macrolide co-administered with denufosol. In such a case, denufosol, the macrolide, or the combination is formulated as a nanosuspension with the carrier loaded with the compounds; such a preparation is then filtered through a fine porous membrane or a suitable filtering medium, or is exposed to solvent interchanges to produce nanoparticles. Such nanoparticulate preparations are freeze-dried or held in suspension in an aqueous or physiologically compatible medium. The preparations so obtained can be inhaled by suitable means.

Another example of a suitable preparation includes a reconstitutable preparation. In this case, denufosol, the macrolide, or the combination is formulated in a preparation to contain the necessary adjuvants to make it physiologically compatible. Such a preparation is reconstituted by addition of water or suitable physiological fluids, admixed by simple agitation and inhaled using appropriate techniques.

Denufosol, the macrolide, or the combination can be prepared into dry powder or equivalent inhalation powders using the well known art of super critical fluid technology. In such a case, denufosol and the macrolide are admixed with appropriate excipients and milled into a homogenous mass using suitable solvents or adjuvants. Following this, this mass is subjected to mixing using super critical fluid technology to achieve suitable particle size distribution. The desired particle size is the size suitable for direct inhalation into the lungs using a suitable inhalation technique, or the size suitable for being introduced into the lungs via a mechanical ventilator. Alternatively, the size is large enough to be admixed with a fluid, wherein the particle dissolves mostly or completely prior to nebulization into the lungs.

To prevent particle size growth and minimize crystal growth of the combination of denufosol and the macrolide, the particle can be spray-dried to have better aerodynamic properties than micronized material.

Another example of a suitable preparation includes a preparation of freeze-dried or lyophilized preparation of denufosol, the macrolide, or the combination. Such a preparation is made to protect the inherent instability of the molecule due to physical or chemical changes induced in the presence of certain solvents or processing techniques. Cryoprotectants can be used to further maintain the physical and chemical stability of denufosol, the macrolide, or the combination. The lypophilized preparations can be used as is in the form of a dry powder inhaler. The lypophilized preparations can also be admixed with other suitable adjuvants and be used as dry powder inhaler or as nebulized preparation.

In one embodiment, the macrolide and denufosol are administered 1, 2, or 3 times a day sequentially (i.e. one after the other), or co-administered together. In general, denufosol is administered at 30-130, or 40-80, or 50-70 mg per dosage, and the macrolide is administered at about 3-70, or 5-50, or 8-30 mg per dosage, when administered three times a day. When the agents are co-administered, the two compounds can be mixed just prior to the administration or they can be admixed as one homogenous mixture in a self contained preparation, provided the physical and chemical stability is maintained. In one embodiment, the macrolide and denufosol are admixed as one pharmaceutical formulation and admistered to patients by inhalation. One single pharmaceutical formulation and one single treatment provide ease of use and result in better compliance of patients.

In another embodiment, denufosol is presented as a formulation suitable for inhalation while the macrolide is presented as a formulation suitable for oral delivery. For example, denufosol is administered 1-3 times a day by inhalation at 30-130, or 40-80, or 50-70 mg per dosage, and the macrolide such as azithromycin is administered orally 1-7 times, preferably 1-5 times, and most preferably 2-4 times per week at 100-500 mg (e.g. about 250 mg) per dosage. The macrolide and denufosol can be administrated to CF patients in addition of other drugs, e.g., bronchodilators, other non-macrolide antibiotics, inhaled tobramycin, alfa dornase, and pancreatic enzyme.

Pharmaceutical Formulation

The present invention is directed to a pharmaceutical formulation comprising denufosol or a pharmaceutically acceptable salt thereof, a macrolide, and a pharmaceutically acceptable carrier. Preferred denufosol is denufosol tetrasodium and preferred macrolide is azithromycin.

The pharmaceutical formulation of the present invention is preferably in a form of an inhalable dry powder or in a liquid form.

When in an inhalable dry powder form, the pharmaceutical formulation comprises about 30-130, or 40-80, or 50-70 mg of denufosol tetrasodium and about 3-70, or 5-50, or 8-30 mg of azithromycin in a unit dosage form. For example, the pharmaceutical formulation comprises about 60 mg of denufosol tetrasodium and 20 mg of azithromycin in a unit dosage form.

When in a liquid form, the pharmaceutical formulation comprises about 5-50, or 10-25 mg/mL of denufosol tetrasodium and about 0.5-8 or 1-4 mg/mL of azithromycin. In one embodiment, the pharmaceutical formulation comprises about 40-100 mg of denufosol tetrasodium and 4-16 mg of azithromycin in about 4 mL, which can be administered to CF patient as a single dosage unit in the form of aerosol for oral inhalation. For example, the pharmaceutical formulation comprises about 60 mg of denufosol tetrasodium and 16 mg of azithromycin in about 4 mL. In another embodiment, the pharmaceutical formulation comprises about 20-50 mg of denufosol tetrasodium and 2-8 mg of azithromycin in about 2 mL, which can also be administered to CF patient as a single dosage unit in the form of aerosol.

Pharmaceutically acceptable carriers include excipients, suspending agents, diluents, fillers, salts, buffers, stabilizers, solubilizers, solvents, dispersion media, coatings, isotonic agents, and other materials known in the art. The pharmaceutical formulation optionally includes potentiators, complexing agents, targeting agents, stabilizing agents, cosolvents, pressurized gases, or solubilizing conjugates.

Acceptable excipients include sugars such as lactose, sucrose, mannitol, or sorbitol; cellulose preparations such as, maize starch, wheat starch, rice starch, potato starch, gelatin, gum tragacanth, methyl cellulose, hydroxypropylmethylcellulose, sodium caroxymethylcellulose, and/or polyvinylpyrrolidone (PVP). Preferred excipients include lactose, gelatin, sodium carboxymethyl cellulose, and low molecular weight starch products.

Acceptable suspending agents that can serve as valve lubricants in pressurized pack inhaler systems are desirable. Such agents include oleic acid, simple carboxylic acid derivatives, and sorbitan trioleate.

Acceptable diluents include water, saline, phosphate-buffered citrate or saline solution, and mucolytic preparations. Other diluents that can be considered include alcohol, propylene glycol, and ethanol; these solvents or diluents are more common in oral aerosol formulations. Physiologically acceptable diluents that have a tonicity and pH compatible with the alveolar apparatus are desirable. Preferred diluents include isotonic saline, phosphate buffered isotonic solutions whose tonicity have been adjusted with sodium chloride or sucrose or dextrose or mannitol.

Acceptable fillers include glycerin, propylene glycol, ethanol in liquid or fluid preparations. Suitable fillers for dry powder inhalation systems include lactose, sucrose, dextrose, suitable amino acids, and derivatives of lactose. Preferred fillers include glycerin, propylene glycol, lactose and certain amino acids.

Acceptable salts include those that are physiologically compatible and provide the desired tonicity adjustment. Monovalent and divalent salts of strong or weak acids are desirable. Preferred salts include sodium chloride, sodium citrate, ascorbates, sodium phosphates.

Acceptable buffers include phosphate or citrate buffers or mixed buffer systems of low buffering capacity. Preferred buffers include phosphate or citrate buffers.

Acceptable coating agents to provide a hydrophobic sheath around the hydrophilic cores could include caproic and lauric acids. During the preparation of liposomes the use of diphosphatidyl choline or diphosphatidyl myristyl choline or suitable such mixtures can be considered to provide protection to the molecules or formulation.

Acceptable stabilizers include those that provide chemical or physical stability of the final preparations. Such stabilizers include antioxidants such a sodium metabisulfite, alcohol, polyethylene glycols, butylated hydroxyanisole, butylated hydroxytoluene, disodium edetate. Preferred stabilizers include sodium metabisulfite, disodium edetate and polyethylene glycols. Included within this class of stabilizers would be cryoprotectants such as polyethylene glycols, sugars, and carrageenans.

Acceptable solubilizers include propylene glycol, glycerin, suitable amino acids, complexing agents such as cyclodextrins, sorbitol solution, or alcohol. Solubilizers including ethanol, propylene glycol, glycerin, sorbitol, and cyclodetrins are desirable. Preferred solubilizers include propylene glycol, sorbitol, and cyclodextrins.

The active ingredients can be formulated for inhalation with use of a suitable propellant such as dichlorodifluoromethane, dichloroflouromethane, dichlorotetrafluoroethane, carbon dioxide or other gas. Preferred propellants include non-CFC related class of propellants or related analogs.

The active indegredients can also be dried into an inhalable dry powder. This can be achieved by mixing with suitable adjuvants that are compatible with the macrolide and denufosol and offer biological compatibility. Desirable methods of drying the pharmaceutical material for inhalation include spray drying, conventional bed drying, or super critical fluid processing; with spray drying and super critical fluid processing being preferred.

Packaging

Denufosol and the macrolide can be packaged individually so to allow a practitioner to formulate each into a pharmaceutical composition as needed. Alternatively, the pharmaceutical composition comprising denufosol and the macrolide can be packaged, thereby requiring de minimus formulation by practitioner. In any event, the packaging should maintain chemical, physical, and aesthetic integrity of the active ingredients.

Possible methods of packaging include blister packaging, packaging in unit dose vials, packaging in blow-fill-seal plastic vials, filling in pressurized canisters, packaging in a two compartment system wherein the contents of the two compartments are admixed by mechanical agitation prior to administration and the contents used within a specified period of time. Packaging the material by filling into a plastic vial whose contents can be easily opened, contents dispensed, and empty container disposed off to prevent re-use or contamination is deemed advantageous. The most preferred packaging method is packaging the formulation in a blister packaging system wherein the contents are held protected from heat, light, and other environmental extremes.

Where the therapeutic material is packaged for inhalation, the pharmaceutical composition can be packaged in an aerosol spray canister or packaged for use with a nebulizer or ventilator. This can be achieved by directly filling the container using the common technique of cold filling, or filling under a pressurized system, or simply filling the product formulation under gravity feed in an aseptic environment. Depending on the nature of the final formulation, this can be preferably achieved by a cold-filling technique, wherein the composition is packaged in an aerosol canister under high pressure in a clean-room environment, preferably under aseptic conditions. Alternatively, if the composition is a simple solution, homogenous fluid, or well-mixed suspension product, the formulation can be filled into unit dose blow-fill-seal vials under a gravity feed or filled into blister packs wherein the formulation is filled into unit cavities and secured close with suitable foil or equivalent packaging to protect it from environmental extremes. This operation is preferred to be carried out under aseptic conditions, preferably under ambient or sub-ambient temperatures with little to no environmental extremes. It is important that such filling and packaging operations be conducted in relatively particulate- free environments with minimal microbiological loads (especially absence of *Pseudomonas* and other similar pathogens) and be done with minimal exposure to direct human interface. The blister packaging can be done most optimally with cold fill packaging. The product compositions can be directly filled into the final container of choice by direct metered transfer (either gravimetrically or volumetrically) and secured close with appropriate closure systems.

Advantages of the Present Invention

The inventors have discovered that the combined administration of denufosol and a macrolide to a cystic fibrosis patient has several advantages that cannot be achieved by a single administration of either denufosol or a macrolide.

Macrolides are known to have side effects related to gastrointestinal, cardiovascular, genitourinary, CNS effects (such as dizziness and headache), and allergic reaction. When denufosol and a macrolide are administered together to a patient suffering from CF, the dosage of the macrolide is reduced, thus reducing or eliminating the dose-related side effects of the macrolide. A combined administration of a macrolide and denufosol is more effective than a single administration of the macrolide or denufosol in treating cystic fibrosis. The inventors have noted that not any medications of cystic fibrosis can be combined to provide additive therapeutic effects (see the results of Table 3).

The inventors have also discovered that inhalation is an effective method for delivering denufusol and the macrolide. Inhalation is a localized administration method and can therefore be more effective in reaching the target area, i.e., the lung, and providing a high and localized concentration of denufosol and the macrolide. Inhalation avoids undesired side effects due to systemic exposure of the macrolide and reduces the risk of patients from developing antibiotic resistance.

Further Embodiment

The present invention is further directed to a method for treating cystic fibrosis, comprising the steps of: first identifying a patient suffering from cystic fibrosis, and then administering to the patient an effective amount of denufosol and an effective amount of an antibiotic by inhalation. The inhaled antibiotics suitable for the present invention include inhaled aminoglycosides (tobramycin), inhaled fluoroquinolones (ciprofloxacin, moxifloxacin, gatifloxacin), inhaled beta-lactam (aztreonam), inhaled polymixin E antibiotics (colistin) and inhaled ketolide antibiotics (telithromycin and cethromycin).

The invention is illustrated further by the following examples that are not to be construed as limiting the invention in scope to the specific procedures described in them.

EXAMPLES

Example 1

Test Design

This is a multi-center, double-blind, randomized, efficacy and safety study of denufosol in patients with mild CF lung disease. Approximately 350 patients were enrolled and randomly assigned to receive one of two treatments, 60 mg denufosol TID or placebo TID, with approximately 175 patients assigned to each treatment group. Patients were administered study drug (denufosol) or placebo using the PARI LC STAR™ nebulizer and PART PRONEB Ultra™ compressor. At the end of the 24-week double-blind, placebo-controlled treatment period, placebo patients received 60 mg denufosol for a 24-week safety extension period. All patients on denufosol during the first 24 weeks continued to receive denufosol during the 24-week safety extension. Upon completion of study participation or discontinuation from study treatment, all patients were scheduled for a 1-week follow-up visit. The clinical study schematic is shown in FIG. 1.

Subjects

Subjects were >5 years of age and had a confirmed diagnosis of CF (positive sweat chloride value >60 mEq/L, and/or genotype with two identifiable mutations consistent with CF, accompanied by one or more clinical features consistent with the CF phenotype). Subjects had a forced expiratory volume at one second (FEV1) >75% of predicted normal for age, gender, and height.

In general, CF patients took many medications as their usual standard of care. This study was designed to randomly assign patients either to denufosol or placebo on top of their usual standard of care. Table 1 shows the percentages of subjects in this study who used various CF medications at base line. Patients were instructed whenever possible to use these medications consistently throughout the study.

TABLE 1

Demographic and Background Data at base line

| | | Placebo (N = 174) | Denufosol 60 mg (N = 178) | Total (N = 352) |
|---|---|---|---|---|
| Bronchodilator User | No | 37 (21.3%) | 32 (18.0%) | 69 (19.6%) |
| | Yes | 137 (78.7%) | 146 (82.0%) | 283 (80.4%) |
| Chronic Inhaled Antibiotic User | No | 108 (62.1%) | 113 (63.5%) | 221 (62.8%) |
| | Yes | 66 (37.9%) | 65 (36.5%) | 131 (37.2%) |
| Chronic Inhaled Tobramycin User | No | 109 (62.6%) | 117 (65.7%) | 226 (64.2%) |
| | Yes | 65 (37.4%) | 61 (34.3%) | 126 (35.8%) |
| Pulmozyme User | No | 40 (23.0%) | 41 (23.0%) | 81 (23.0%) |
| | Yes | 134 (77.0%) | 137 (77.0%) | 271 (77.0%) |
| Macrolide User | No | 104 (59.8%) | 109 (61.2%) | 213 (60.5%) |
| | Yes | 70 (40.2%) | 69 (38.8%) | 139 (39.5%) |
| Pancreatic Enzyme User | No | 9 (5.2%) | 19 (10.7%) | 28 (8.0%) |
| | Yes | 165 (94.8%) | 159 (89.3%) | 324 (92.0%) |

Test Protocols

All patients were instructed to inhale the study drug using normal tidal breathing via the PARI LC STAR™ reusable nebulizer and the PARI PRONEB™ Ultra compressor. A dose was considered complete after 15 minutes of inhalation or when the nebulizer sputters. Study drug was taken TID at the same time each day.

Assessment of Efficacy

Primary efficacy endpoint was change in lung function, as measured by FEV1 (L), from baseline to Week 24 end point. Missing Week 24 data for patients who withdrew prior to Week 24 were imputed from the last available observation carried forward. Secondary efficacy endpoints included the following: time to first pulmonary exacerbation during the 24-week placebo-controlled treatment period; incidence of pulmonary exacerbations during the 24-week placebo-controlled treatment period; number of pulmonary exacerbations/time at risk (incidence density) during the 24-week placebo-controlled treatment period; change in lung function, as measured by FEV1 (L) from baseline to Weeks 4 and 12, and FVC (L) and FEF25%-75% (L/sec) from baseline to Weeks 4, 12, 24, and the end point. Other secondary efficacy endpoints include incidence of IV antibiotic use during the 24-week placebo-controlled treatment period; number of days of IV antibiotic use during the 24-week placebo-controlled treatment period; incidence of new use of antipseudomonal antibiotics during the 24-week placebo-controlled treatment period; incidence of hospitalizations/ER visits for a respiratory-related complaint during the 24-week placebo-controlled treatment period; number of days spent in the hospital for a respiratory-related complaint during the 24-week placebo-controlled treatment period; changes from baseline to Weeks 12 and 24 in Health-related Quality of Life as measured by the Cystic Fibrosis Questionnare and the Feeling Thermometer; and changes in utility assessment from baseline to Weeks 12 and 24 as measured by the Health Utilities Index; number of CF-related days lost from work or school during the 24-week placebo-controlled treatment period; and responses at Week 24 to the Patient Questionnaire.

Results

1. Macrolide Users 70 patients in the placebo group and 69 patients in the denufosol group used macrolides as one of their usual standard of care. In the macrolide users, 97% took azithromycin, and the remaining took clarithromycin or erythromycin. In the macrolide users, the adjusted means for change in lung function, as measured by FEV1, from baseline to Week 24, was −0.0457 (L) for the placebo group and 0.0288 (L) for the denufosol group. The p-value was 0.047. An improvement of +0.0745 (L) was seen in the macrolide group when they were treated with denufosol.

Many of the macrolide users also took pulmozyme and other non-macrolide antibiotics as their usual standard of care. To compare the therapeutic effects of a single drug denufosol, macrolide, and pulmozyme, versus the combination of denufosol and macrolide and the combination of pulmozyme and macrolide, the analysis of subgroup data was performed.

2. Subset Data (Denufosol/Macrolide)

Figure 2:
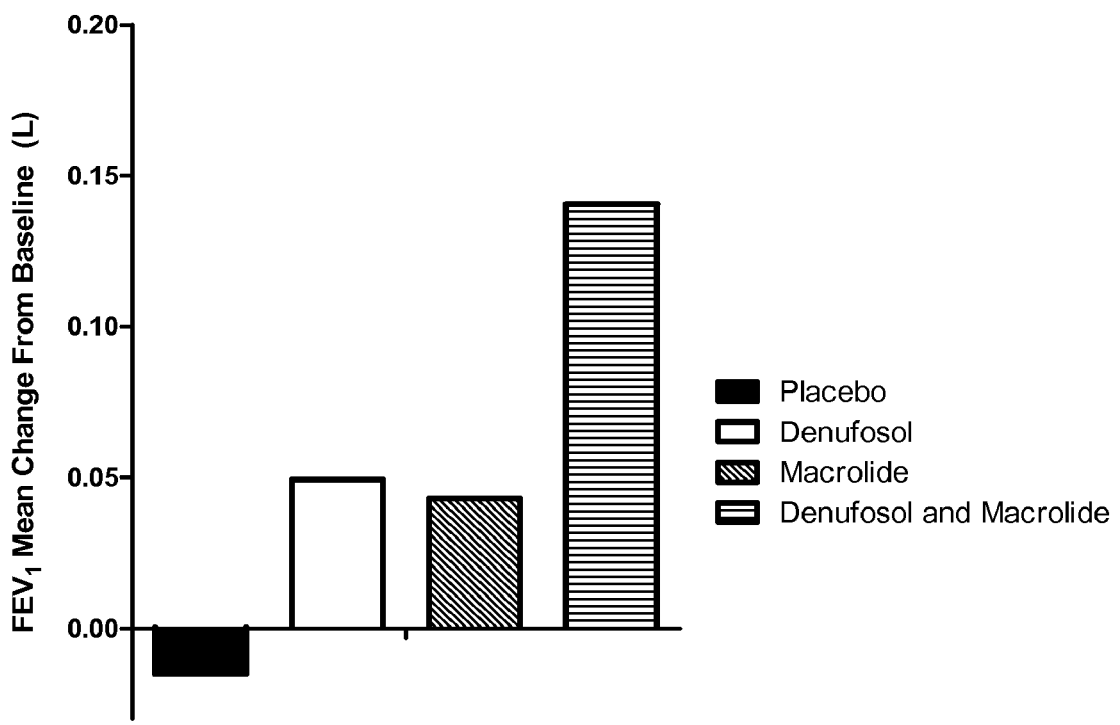
FIG. 2 shows the mean change of FEV1 (L) from baseline to Week 24 in subgroups of patients treated with placebo, denufosol alone, macrolide alone, and denufosol plus macrolide.

Data of subgroups that did not take pulmozyme or inhaled antibiotics were analyzed. The mean change from baseline to Week 24 in patients treated with placebo, denufosol alone, macrolide alone, and denufosol plus macrolide were compared in terms of FEV1 (L). The results are shown in Table 2 and FIG. 2.

TABLE 2

FEV$_1$ Change from baseline in Liters

| Treatment | Number of Patients | Mean | Standard Deviation |
|---|---|---|---|
| Placebo | 24 | −0.0152 | 0.2037 |
| Denufosol | 27 | 0.0494 | 0.1559 |
| Macrolide (Azithromycin) | 5 | 0.0430 | 0.2305 |
| Denufosol and macrolide (Azithromycin) | 10 | 0.1405 | 0.1769 |

The results showed a numerical trend that the combination of oral macrolide and inhaled denufosol provided a better treatment of cystic fibrosis than oral macrolide alone or inhaled denufosol alone.

3. Subset Data (Pulmozyme/Macrolide)

Figure 3:
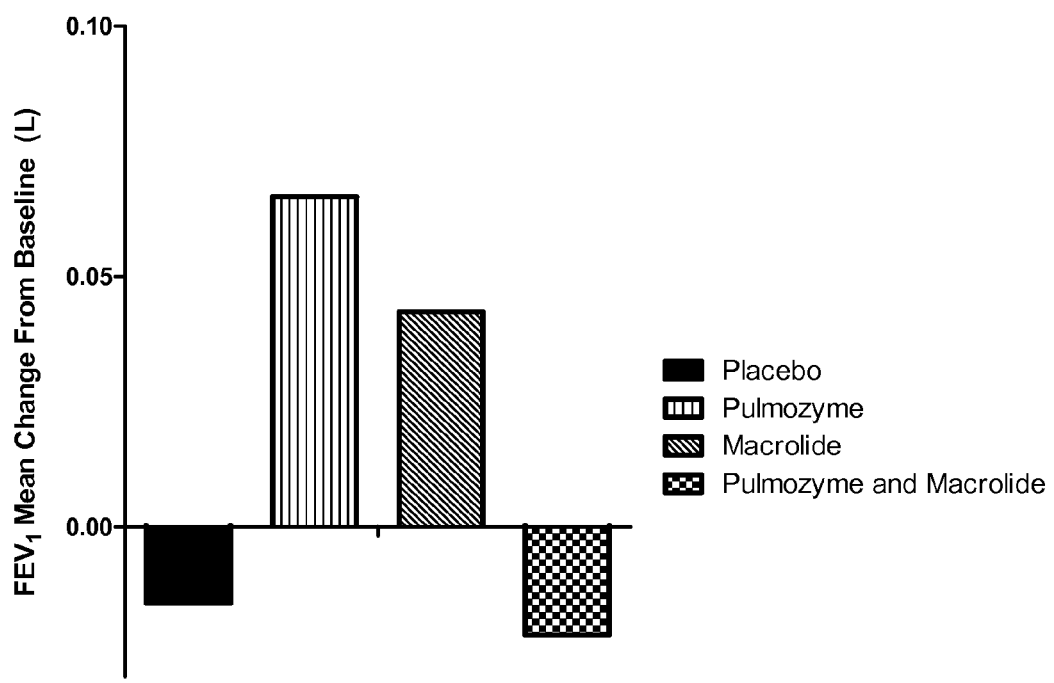
FIG. 3 shows the mean change of FEV1 (L) from baseline to Week 24 in subgroups of patients treated with placebo, denufosol alone, pulmozyme alone, and denufosol plus pulmozyme.

Data of subgroups that did not take pulmozyme or inhaled antibiotics were analyzed. The mean change from baseline to Week 24 in patients treated with placebo, pulmozyme alone, macrolide alone, and pulmozyme plus macrolide were compared in terms of FEV1 (L). The results are shown in Table 3 and FIG. 3.

TABLE 3

FEV$_1$ Change from baseline in Liters

| Treatment | Number of Patients | Mean | Standard Deviation |
|---|---|---|---|
| Placebo | 24 | −0.0152 | 0.2037 |
| Pulmozyme | 51 | 0.0659 | 0.1780 |
| Macrolide (Azithromycin) | 5 | 0.0430 | 0.2305 |
| Pulmozyme and Macrolide (Azithromycin) | 28 | −0.0216 | 0.2169 |

The results show a numerical trend that the combination of oral macrolide and pulmozyme provided a worse treatment of cystic fibrosis than oral macrolide alone or pulmozyme alone.

The results indicate that not any medications of cystic fibrosis can be combined to provide an additive therapeutic effect.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications can be made therein without departing from the scope of the present invention as set forth in the claims. To particularly point out and distinctly claim the subject matter regarded as invention, the following claims conclude this specification.

What is claimed is:

1. A method for treating cystic fibrosis, comprising the steps of:
    identifying a patient suffering from cystic fibrosis,
    administering to the patient an effective amount of denufosol or a pharmaceutically acceptable salt thereof and an effective amount of a macrolide.

2. The method according to claim 1, wherein the denufosol is administered by inhalation.

3. The method according to claim 2, wherein the macrolide is administered by oral administration or inhalation.

4. The method according to claim 1, wherein said denufosol is denufosol tetrasodium.

5. The method according to claim 1, wherein said denufosol and the macrolide are co-administered.

6. The method according to claim 1, wherein said denufosol and the macrolide are co-administered in a single pharmaceutical formulation by inhalation.

7. The method according to claim 1, wherein said macrolide is selected from the group consisting of azithromycin, clarithromycin, dirithromycin, erythromycin, and roxithromycin.

8. The method according to claim 7, wherein said macrolide is azithromycin.

9. The method according to claim 1, wherein the effective amount of denufosol is about 100-400 mg per day and an effective amount of a macrolide is 10-200 mg per day.

10. A pharmaceutical formulation comprising denufosol or a pharmaceutically acceptable salt thereof, a macrolide, and a pharmaceutically acceptable carrier.

11. The pharmaceutical formulation according to claim 10, wherein said denufosol is denufosol tetrasodium and said macrolide is azithromycin.

12. The pharmaceutical formulation according to claim 10, which is in a form of an inhalable dry powder.

13. The pharmaceutical formulation according to claim 12, comprising about 30-130 mg of denufosol tetrasodium and about 3-70 mg of azithromycin in a unit dosage form.

14. The pharmaceutical formulation according to claim 10, which is in a liquid form.

15. The pharmaceutical formulation according to claim 14, comprising about 5-50 mg/mL of denufosol tetrasodium and about 0.5-8 mg/mL of azithromycin.

* * * * *